(12) United States Patent
Persson et al.

(10) Patent No.: US 9,427,494 B2
(45) Date of Patent: Aug. 30, 2016

(54) FIBRE-BASED SURGICAL IMPLANT AND METHOD OF MANUFACTURE

(75) Inventors: Anders Persson, Gothenburg (SE); Eugenio Ferrario, Gothenburg (SE)

(73) Assignee: INTERNATIONAL LIFE SCIENCES, LLC, Nashville, TN (US)

( * ) Notice: Subject to any disclaimer, the term of this patent is extended or adjusted under 35 U.S.C. 154(b) by 636 days.

(21) Appl. No.: 12/863,242

(22) PCT Filed: Jan. 16, 2009

(86) PCT No.: PCT/SE2009/000016
§ 371 (c)(1),
(2), (4) Date: Sep. 16, 2010

(87) PCT Pub. No.: WO2009/093954
PCT Pub. Date: Jul. 30, 2009

(65) Prior Publication Data
US 2011/0046742 A1     Feb. 24, 2011

(30) Foreign Application Priority Data
Jan. 21, 2008   (SE) ...................................... 0800139

(51) Int. Cl.
*A61L 27/18*   (2006.01)
*A61F 2/30*    (2006.01)
(Continued)

(52) U.S. Cl.
CPC ............. *A61L 27/18* (2013.01); *A61F 2/30756* (2013.01); *A61L 27/56* (2013.01); *A61L 27/58* (2013.01); *D04B 21/16* (2013.01); *A61F 2/3094* (2013.01); *A61F 2002/30008* (2013.01); *A61F 2002/30065* (2013.01); *A61F 2002/30077* (2013.01); *A61F 2002/3096* (2013.01); *A61F 2002/30172* (2013.01); *A61F 2002/30616* (2013.01); *A61F 2002/30878* (2013.01); *A61F 2002/4495* (2013.01); *A61F 2210/0066* (2013.01);
(Continued)

(58) Field of Classification Search
CPC ....................................................... A61L 27/18
USPC ....................................................... 623/11.11
See application file for complete search history.

(56) References Cited

U.S. PATENT DOCUMENTS 3,317,924 A   5/1967   Le Veen et al.
3,945,052 A   3/1976   Liebig
(Continued)

FOREIGN PATENT DOCUMENTS

EP   0 505 634 A1   9/1992
EP   1 351 630 B1   3/2006
(Continued)

OTHER PUBLICATIONS

International Search Report, dated Jun. 12, 2009, from corresponding PCT application.

*Primary Examiner* — David Bates
*Assistant Examiner* — Olivia C Chang
(74) *Attorney, Agent, or Firm* — David G. Rosenbaum; Rosenbaum IP, P.C.

(57) ABSTRACT

A fiber-based surgical implant stabilized against fraying, includes a thermally crimped flat-knitted fabric of a biocompatible, optionally biodegradable, polymer material having a glass transition temperature or other thermally induced secondary conformational mobility threshold in the temperature range of from 20° C. to +170° C. Also disclosed is a corresponding fabric and methods of producing the implant and the fabric.

29 Claims, 8 Drawing Sheets

(51) Int. Cl.
   *A61L 27/56* (2006.01)
   *A61L 27/58* (2006.01)
   *D04B 21/16* (2006.01)
   *A61F 2/44* (2006.01)

(52) U.S. Cl.
   CPC  *A61F2210/0071* (2013.01); *A61F 2230/0052* (2013.01); *A61F 2250/0017* (2013.01); *D10B 2509/08* (2013.01); *Y10T 428/24636* (2015.01)

(56) References Cited

U.S. PATENT DOCUMENTS 5,004,474 A * 4/1991 Fronk et al. ............... 623/13.14
6,093,205 A 7/2000 McLeod et al.
7,037,342 B2 5/2006 Nilsson et al.
2003/0094019 A1 5/2003 Miyake et al.
2006/0058862 A1 3/2006 Dong et al.
2006/0271157 A1* 11/2006 Edens et al. ............... 623/1.13

FOREIGN PATENT DOCUMENTS

| | | |
|---|---|---|
| GB | 892 980 A | 4/1962 |
| GB | 1 299 963 A | 12/1972 |
| WO | 95/25550 A1 | 9/1995 |
| WO | 02/054992 A1 | 7/2002 |

* cited by examiner

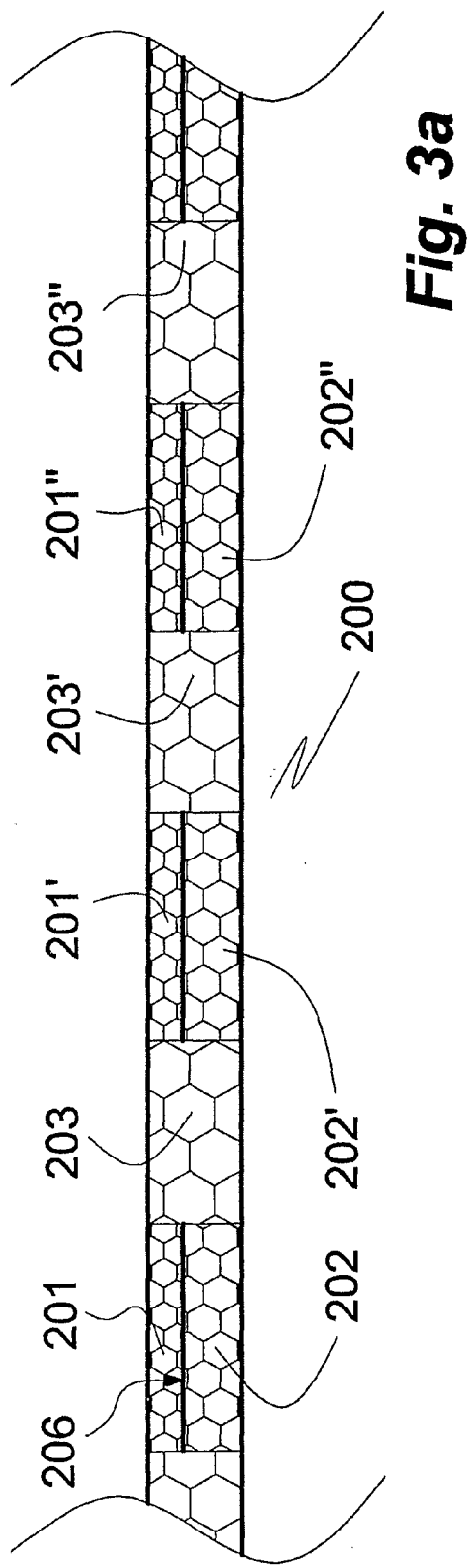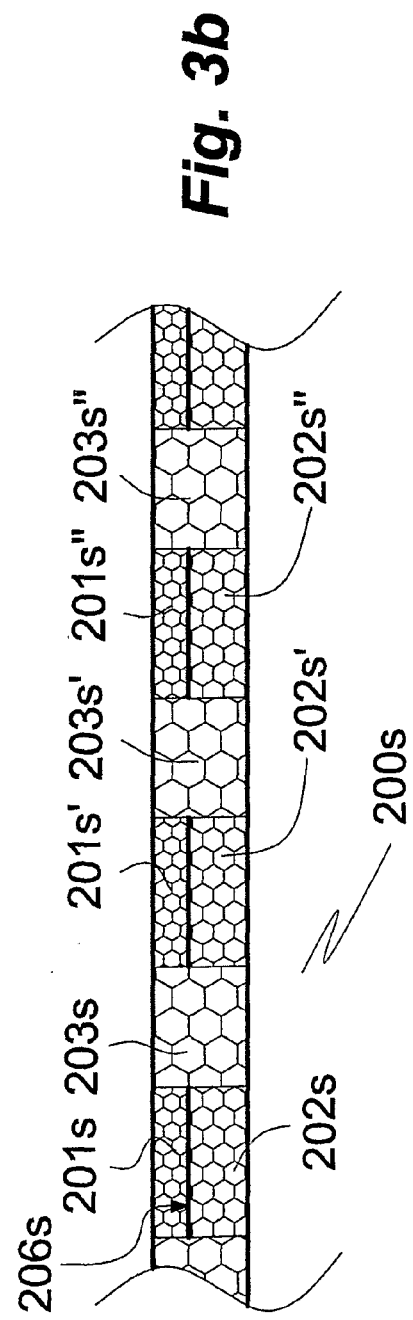

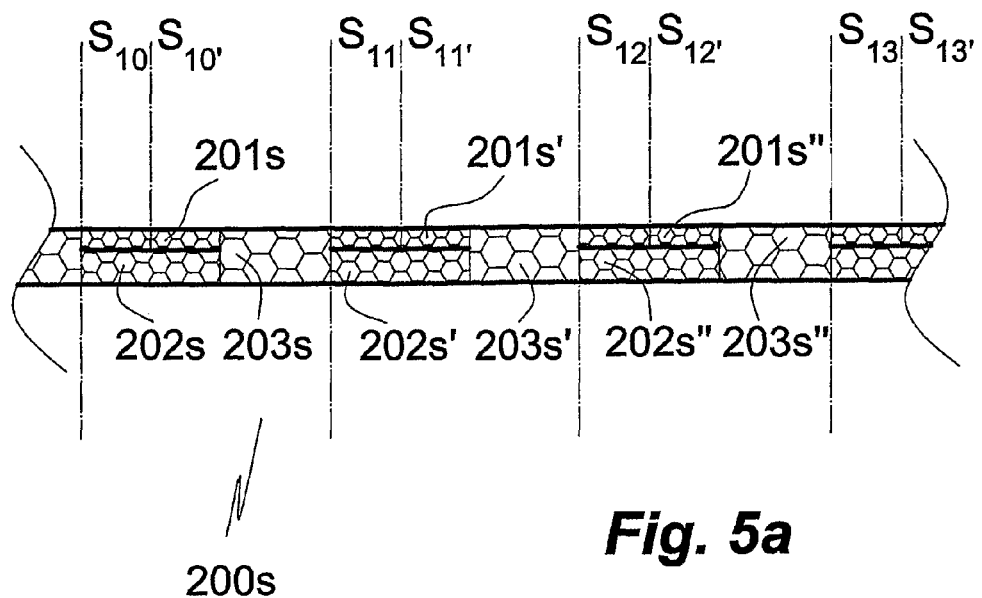
*Fig. 5a*
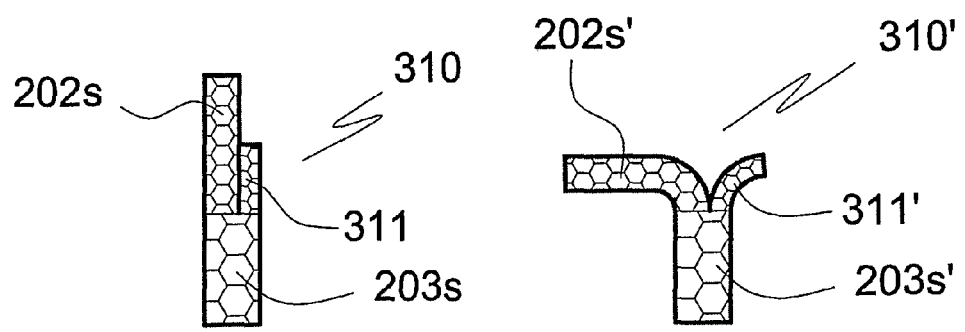
*Fig. 5*  *Fig. 5b*

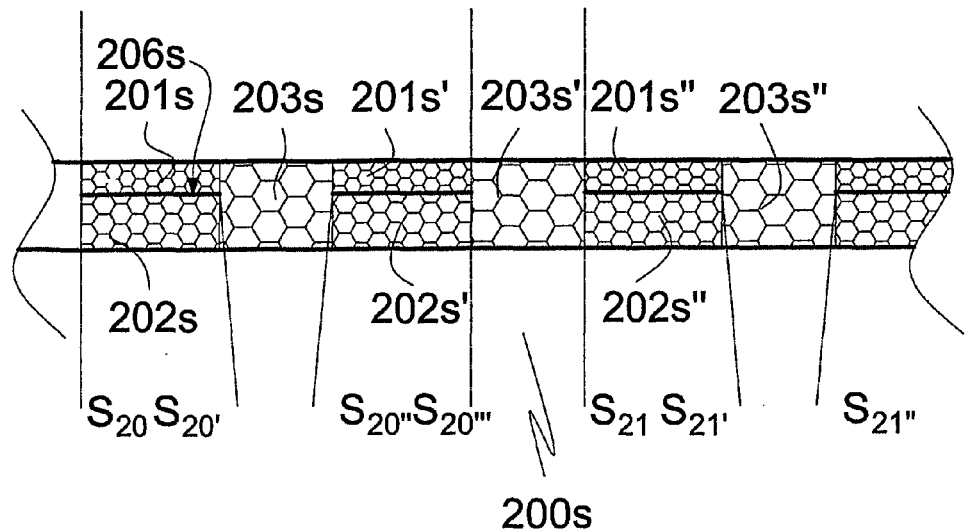
Fig. 6a
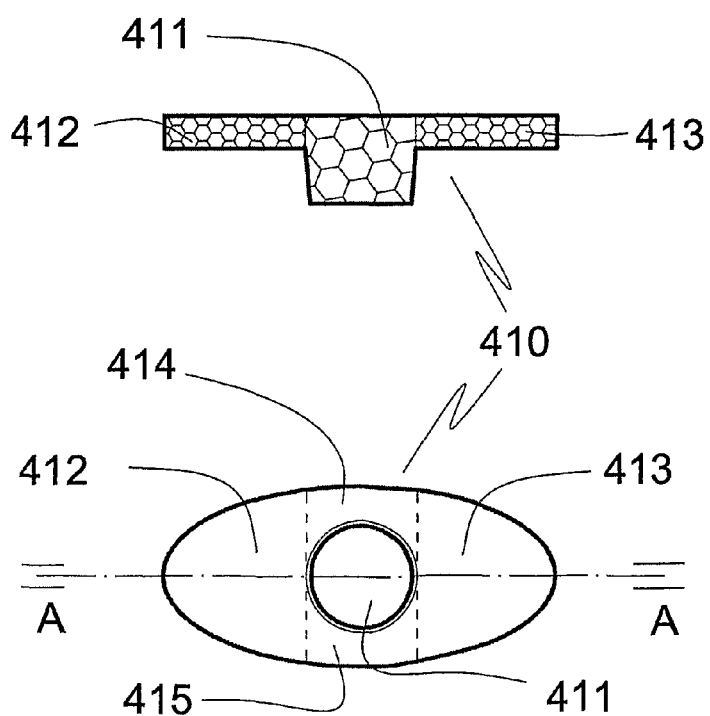
Fig. 6
Fig. 6b

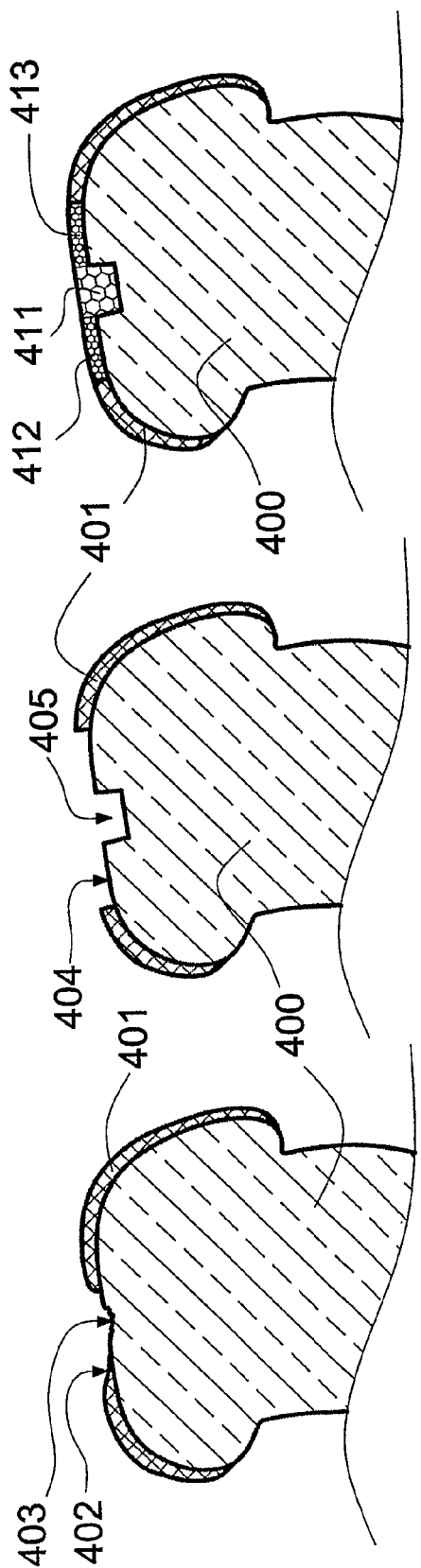

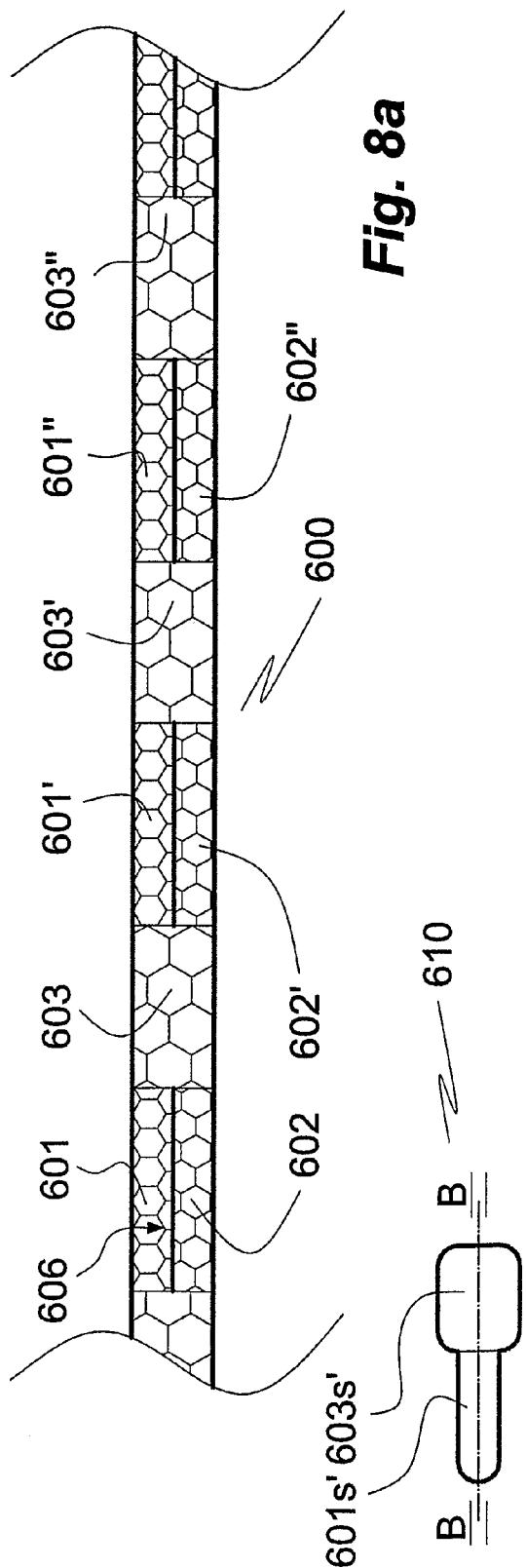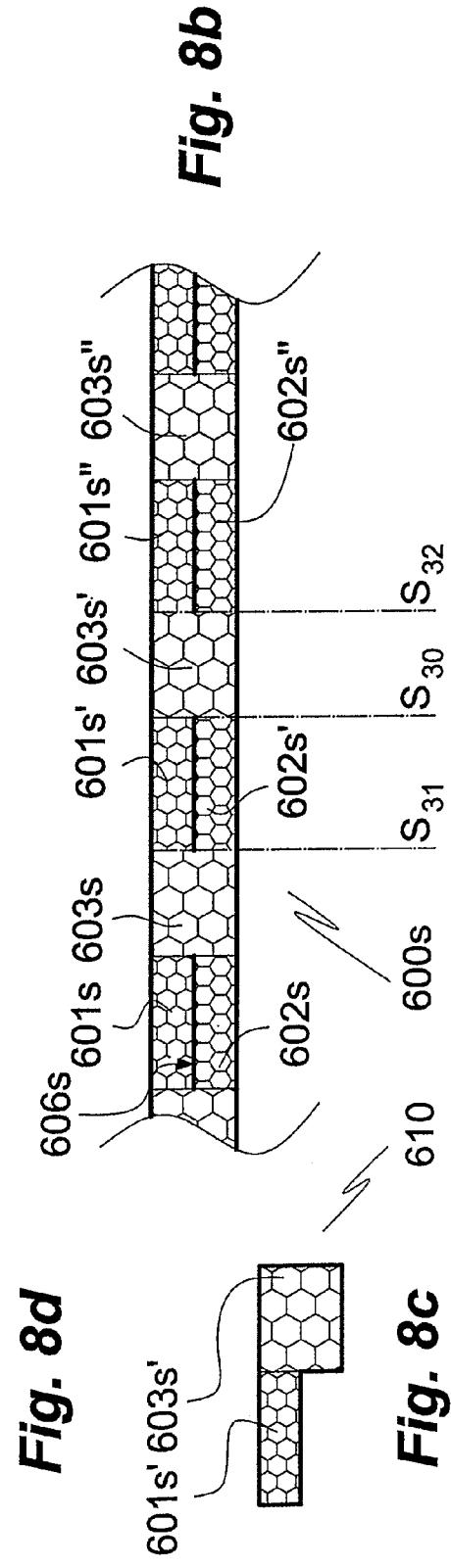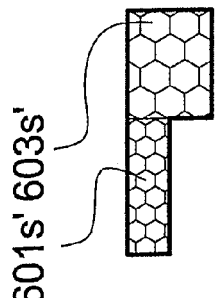

FIBRE-BASED SURGICAL IMPLANT AND METHOD OF MANUFACTURE

FIELD OF THE INVENTION

The present invention relates to a fibre-based surgical implant, a fabric for use in the manufacture of the implant, and methods for producing the fabric and the implant.

BACKGROUND OF THE INVENTION

A wide range of fibre-based surgical implants are known in the art. To be tolerated by the organism an implant has to be biocompatible. Certain uses additionally benefit from the implant being made of or comprising biodegradable material. Fibres for use in biocompatible implants are, in particular, made from suitable synthetic polymers. The fibres of an implant can be disposed in form of an ordered pattern, such as in a woven or knitted textile material, or in a non-ordered pattern, such as in a non-woven textile material. Surgical implants comprising knitted materials are disclosed, for instance, in U.S. Pat. No. 6,093,205 A, EP 505 634 B1, and EP 1 351 630 B1.

For economic reasons a textile fabric for use in implants would benefit from being manufactured in a size allowing the production of multiple implants or implant elements from it. The implants or elements for use in implants would have to be cut out from the fabric. Depending on the production method and textile pattern of the fabric, the degrees of cutting freedom may be restricted by the risk of compromising the integrity of the products by the textile material unraveling or fraying at cut edges. The problem may be aggravated by movements of tissue disposed adjacent to an implant in situ. A common fixation mode for textile implants is by suture(s) penetrating the implant near its fringe(s). Tearing by the suture(s) on implant is an important cause of fraying and of such implants losing their attachment to the respective bone or soft tissue. Fraying of an implanted textile material may cause a malign biological response of host tissue by mechanically induced inflammation and/or particle synovitis. In consequence the implant might require explantation. To avoid the risk of fraying woven fabrics for implant applications should not be cut along the warp. One commercially available woven fabric implant comprised by this restriction is the Artelon® TMC Spacer (Nilsson et al., J Hand Surg, 2005; 30A(2) 380-9). Hence, the dimensions of a manufactured implant of this kind will have to be a compromise in view of the need to make an implant of given form and size fit as many patients as possible. Although a woven implant may be available in different sizes its case-by-case refined biometric and anatomic adaptation would be desirable. With a textile design that permits unrestricted cutting in the plane of the fabric a ready-made implant could be supplied with a shape better adapted to anatomical and biometric requirements. Even a final tailoring by the surgeon can be enabled during surgery. The need of adapting a ready-made implant to a patient is particularly pronounced if it is a part of an articular joint surface that needs treatment. In that case it is a definite benefit if the implant can be trimmed by the surgeon or assisting medical personnel. Fraying of a textile implant thus should be avoided by all means.

OBJECTS OF THE INVENTION

An object of the invention is to provide a textile material of the aforementioned kind having little or no tendency to fray at cut edges thereof.

Another object of the invention is to provide a surgical implant comprising or consisting of such non-fraying textile material.

A further object of the invention is to provide methods of producing a non-fraying textile material and a corresponding implant.

Additional objects of the invention will become evident from the following summary of the invention, preferred embodiments thereof illustrated in a drawing, and the appended claims.

SUMMARY OF THE INVENTION

According to a first aspect of the present invention is disclosed fibre-based surgical implant of the aforementioned kind stabilized against fraying at a cut edge. The fibres of the implant are comprised by a flat-knitted fabric of a biocompatible, optionally biodegradable, polymer material. The polymer material is one capable of being thermally crimped. A measure of this capacity is that the polymer has a glass transition temperature, in particular one of from 20° C. to 170° C. However, there are also polymer materials that can be thermally crimped but do not exhibit a distinct glass transition temperature; within the same temperature range these materials do however exhibit at least one thermally induced conformational mobility threshold that is not a melting threshold, i.e. is a threshold of a secondary not a primary transition. One important polymer material of this kind is poly(urethane urea).

The implant of the invention may comprise fibres of more than one thermally shrinkable polymer material. The implant of the invention may also comprise fibres of varying thickness and/or fibre threads.

An optimal stabilizing effect is achieved by selecting polymer fibres that can be thermally crimped and a knitting pattern that makes the fibres interlock by their crimping action. The fabric may be crimped by, for instance, running it over heated roller(s). Crimping by means of heated cylindrical rollers will preserve the flatness of the fabric. Alternatively the fabric may be thermally crimped to give a non-flat form. This can be accomplished by, for instance, making the fabric abut a heated surface that is not flat, such as a heated concave metal surface. A fabric holder that negatively mirrors the geometry of the heated non-flat surface may be used to press the tissue gently against the heated surface to make the fabric adopt the form of the non-flat surface during the crimping process.

"Cut edge" is an edge formed by a cutting operation, such as by excision or punching. The cutting operation may be carried out in an automated fashion in the course of industrial production or manually at bedside by the use of a pair of scissors or a scalpel. The use of laser and particle beam cutting techniques is within the ambit of the invention.

"Knitted fabric" comprises any fabric manufactured by a knitting method, in particular by warp knitting, but does not comprise woven fabrics. Knitting methods useful in the invention are described, i.a., in: D J Spencer. *Knitting technology, a comprehensive handbook and practical guide*. Third edition, Woodhead Publishing Ltd., Cambridge 2001.

"Crimped knitted fabric" is a thermally crimped fabric. Useful crimping ranges according to the invention in a direction along the weft or perpendicular to the weft are from 10% to 70%, in particular from 25% to 60%, more particularly from 35% to 55%, most preferred about 45%. The thickness of the fabric of the invention is less effected by crimping than the width or length of the fabric, and may even increase as a result of crimping.

Useful polymer materials include poly(ortho ester), poly (glycolic acid), poly(lactic acid), poly(glycolic, lactic acid), poly(β-hydroxybutyric acid), poly(imino carbonate), poly (ε-caprolactone), poly(glycolic/lactic acid, ε-caprolactone), poly(ethyleneterephthalate), poly(etheretherketone), poly (urethane urea), polyurethane, polyamide. These useful materials are only given for exemplification. Thus any other biocompatible polymer having a glass transition temperature within the range given above may also be used.

According to a second aspect of the present invention is disclosed a thermally crimped flat knitted fabric of a biocompatible, optionally biodegradable, material. The material is suitable in the manufacture of non-fraying surgical implants by cutting techniques such as excision or punching. The fabric comprises or consists of a polymer material having an ordered domain, in particular a material having a glass transition temperature, in particular one of from 20° C. to 170° C. or a secondary thermally induced conformational mobility threshold within that temperature range.

According to a third aspect of the present invention is disclosed a method of producing a flat knitted fabric for use in the manufacture of a surgical implant stabilized against fraying, comprising: providing one or more fibres of a biocompatible, optionally biodegradable, polymer material having a glass transition temperature, in particular one of from 20° C. to 170° C., or a secondary thermally induced conformational mobility threshold within that range; knitting a flat fabric from the one or more fibres; crimping the fabric thermally. In particular, the method comprises: (a) knitting in parallel superimposed planes a first fabric ribbon and a second fabric ribbon to form a first fabric ribbon section and second fabric ribbon section; (b) interlacing the fibres used in forming said first and second ribbon sections over a selected ribbon length to knit an interlaced ribbon section; repeating steps (a) and (b) for a selected number of times so as to provide an interlaced fabric ribbon comprising a multitude of alternating double ribbon and interlacing ribbon sections.

According to a fourth aspect of the present invention is disclosed a method of producing a surgical implant stabilized against fraying comprising: providing the product of the method of producing a flat-knitted fabric for use in the manufacture of a surgical implant stabilized against fraying; forming the implant from the fabric, in particular by cutting.

According to a fifth aspect of the present invention is disclosed an intraarticular spacer substantially consisting of a crimped flat-knitted fabric of polymer material.

According to a sixth aspect of the present invention is disclosed an intraarticular spacer excised from a crimped flat-knitted fabric of polymer material.

According to a seventh aspect of the present invention is disclosed a flat-knitted fabric obtained or obtainable by the method of the invention.

According to an eight aspect of the present invention is disclosed a surgical implant obtained or obtainable by the method of the invention.

It is within the ambit of the present invention to provide the fabric of the invention or an implant manufactured from the fabric with agents that improve or safeguard its incorporation into living tissue, such as with hormones, in particular growth hormones, antibiotics, cartilage constituents, including cultured cartilage cells, etc. Such agents are well known to the person skilled in the art and need not to be detailed here.

The invention will now be explained in more detail by reference to a number of preferred embodiments illustrated in a drawing. FIGS. 1-1e are photographic views. The other figures are roughly drawn sketches; in the sectional views the thickness of knitted fabric and of implants produced from knitted shrunk fabric is grossly exaggerated for reasons of clarity.

SHORT DESCRIPTION OF THE FIGURES

FIG. 1a is top view of a transverse section a first embodiment of a flat-knitted poly(urethane urea) ribbon, enlarged;

FIG. 1b is a top view of a transverse section of the flat-knitted ribbon of FIG. 1a, after shrinking, enlarged;

FIGS. 1c-1e are top views of standardised implant patches of comprised by a set of patches punched out from the flat-knitted ribbon of FIG. 1b, enlarged;

FIG. 3a is a partial view of a first embodiment of an interlaced double poly(urethane urea) flat-knitted ribbon of the invention comprising interlaced sections separated by non-interlaced sections, in a longitudinal section and enlarged;

FIG. 3b is the interlaced double flat-knitted ribbon of FIG. 3a, after shrinking and in the same enlarged view;

FIG. 5 is a sectional view of another intraarticular spacer implant body of the invention excised from the flat-knitted ribbon of FIG. 3b, enlarged;

FIG. 5a is the double interlaced flat-knitted ribbon of FIG. 3b, in the same enlarged view, with cutting planes for excision of the implant of FIG. 5 indicated;

FIG. 5b is an intraarticular spacer implant of the invention formed for implantation from the implant body of FIG. 5, in the same view;

FIG. 6 is still another intraarticular implant of the invention excised from the flat-knitted ribbon of FIG. 3b, in a sectional view (A-A, FIG. 6b), enlarged;

FIG. 6a is the double flat-knitted ribbon of FIG. 3b, in the same enlarged view, with cutting planes for the excision of the implant of FIG. 6 indicated;

FIG. 6b is a top view of the implant of FIG. 6, enlarged;

FIG. 7a is the diseased head of a joint, in a sectional view, enlarged;

FIG. 7b is the joint head of FIG. 7a prepared for implantation, in the view of FIG. 7a, enlarged;

FIG. 7c is the joint head of FIG. 7b, provided with the implant of FIG. 6, in the view of FIGS. 7a and 7b;

FIG. 8a is a partial view of a second embodiment of an interlaced double poly(urethane urea) flat-knitted ribbon of the invention, in a longitudinal section (B-B, FIG. 8d) and enlarged;

FIG. 8b is the interlaced double flat-knitted ribbon of FIG. 8a, after shrinking and in the same enlarged view, with cutting planes indicated;

FIG. 8c is an intraarticular spacer implant of the invention excised from the flat-knitted ribbon of FIG. 8b, in the same view and enlarged;

FIG. 8d is a top view of the spacer implant of FIG. 8c, enlarged.

DESCRIPTION OF PREFERRED EMBODIMENTS

EXAMPLE 1

Shrunk flat-knitted poly(urethane urea) ribbon. Yarn: 13 Tex poly(urethane urea) (Artelon®, Artimplant AB, Göteborg, Sweden). Equipment: Comez DNB/EL-800 (Comez s.p.A., Cilavegna, Italy) double needle bed crochet machine, for the production of technical and medical articles. Machine specifications: 15 gauge, 6 weft bars, double needle bed, latch needles. Heat set unit: Comez HSD/800 comprising 2 heat-set cylinders.

Figure 1:
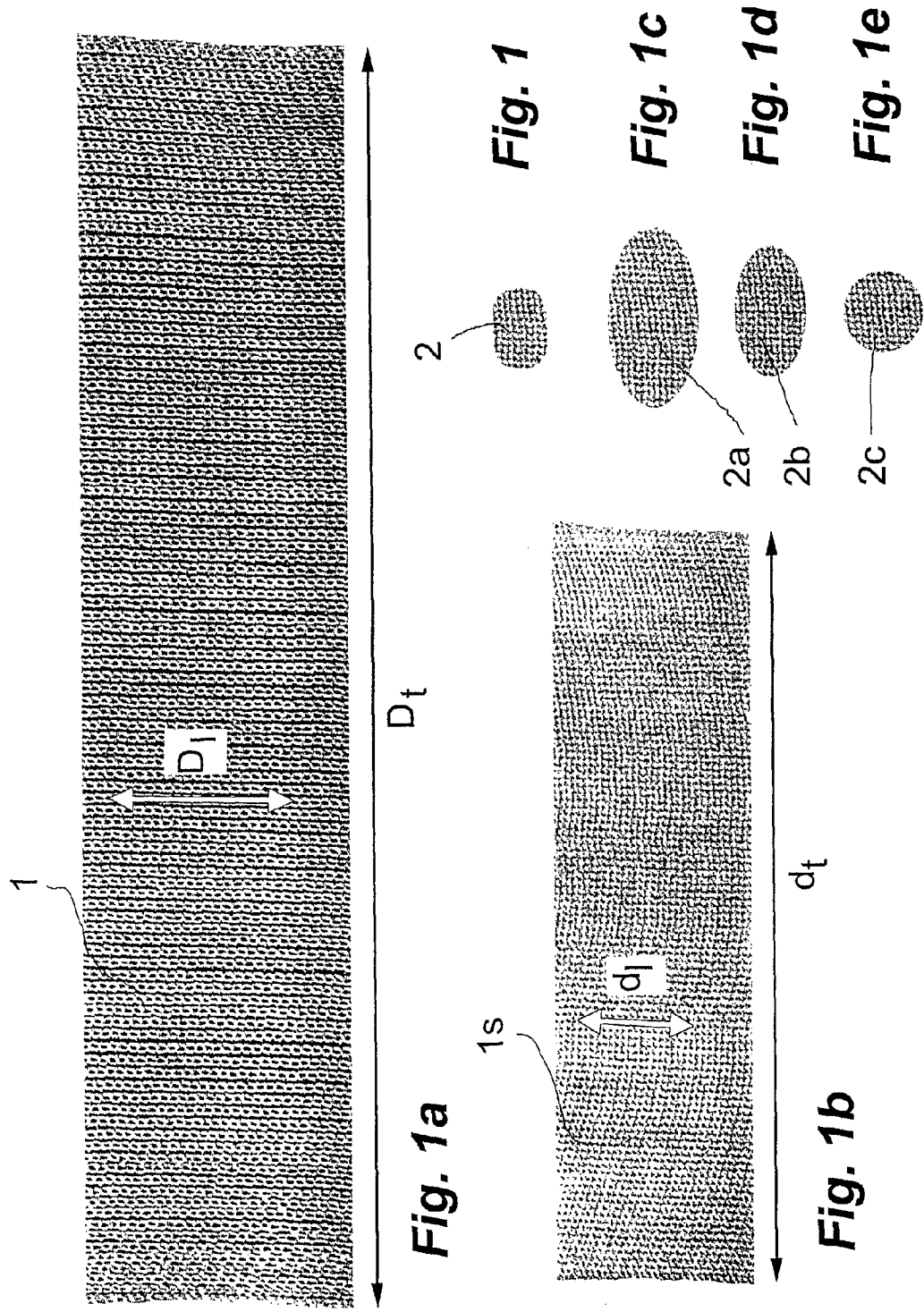
FIG. 1 is a top view of a first embodiment of the implant of the invention, excised from the shrunk flat-knitted ribbon of FIG. 1b or cut to size at bedside from the standardized implant patch of FIG. 1d, enlarged.
Figure 2:
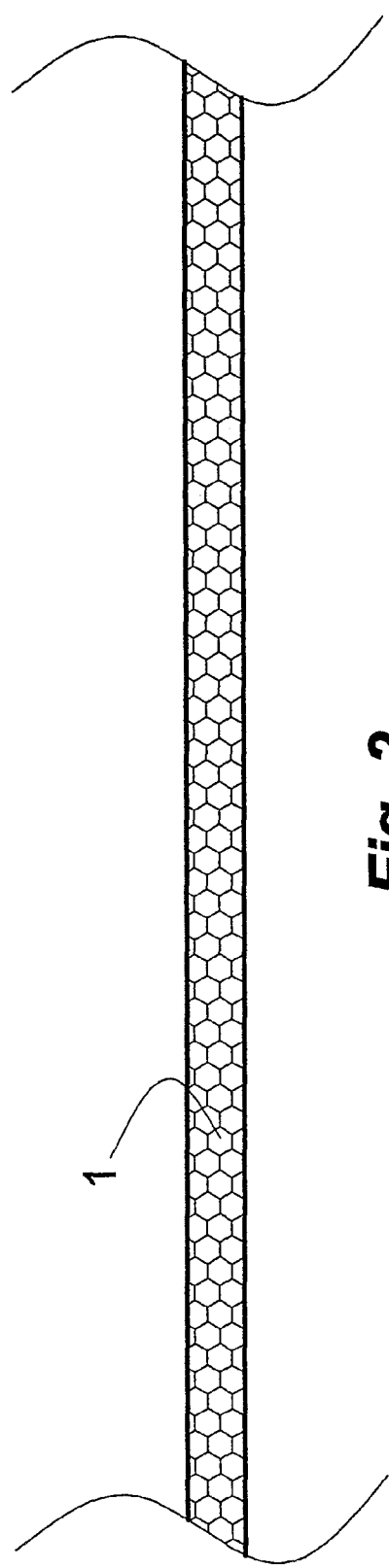
FIG. 2 is a partial view of the flat-knitted ribbon of FIG. 1a, in a longitudinal section and enlarged.
Figure 2A:
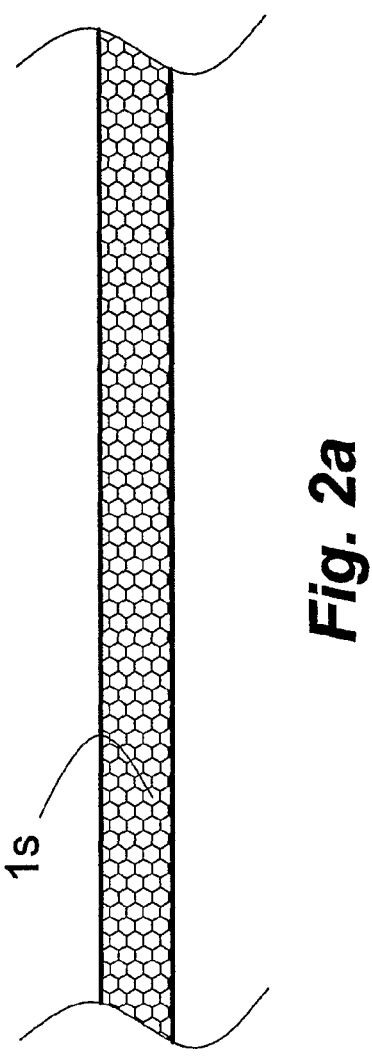
FIG. 2a is a partial view of the flat-knitted ribbon of FIG. 1b, after shrinking; in the same view as that of FIG. 2, enlarged.

A plain ribbon 1 of 14 cm width was knit in the machine (FIGS. 1a, 2). The ribbon 1 was shrunk in the heat set unit at 130° C. to produce a shrunk ribbon 1b a thickness of 0.8 mm (FIGS. 1b, 2a). Process parameters: Knitting speed: 26 cm/min; heat set unit speed: 14 cm/min; shrinkage along warp: about 45% (cf $D_f$, width of ribbon 1 and $d_f$, width of ribbon 1s); shrinkage across warp: about 45% (cf $D_r$, 20 loops, and $d_r$, 20 loops). Warp thickness is slightly increased by shrinking. The warp knitting pattern is shown in Table 1. It is a sequence of four steps with 12 loops/cm.

By using the same parameters and knitting pattern a quadrupled thread gives a shrunk fabric of about 2.0 mm thickness.

TABLE 1

Warp knitting pattern of tricot ribbon

| Loop row | Binding device movement | | | | | | Loops/cm | Alimentation device setting (warp feed) | | | |
|---|---|---|---|---|---|---|---|---|---|---|---|
| | 2 | | 4 | | 5 | | | | | | |
| 1 | 2 | 2 | 3 | 3 | 2 | 2 | 12.00 | 1490 | 2610 | 1790 | 1450 |
| 2 | 2 | 1 | 2 | 1 | 2 | 3 | 12.00 | 1490 | 2610 | 1790 | 1450 |
| 3 | 1 | 1 | 3 | 3 | 2 | 2 | 12.00 | 1490 | 2610 | 1790 | 1450 |
| 4 | 1 | 2 | 4 | 5 | 2 | 1 | 12.00 | 1490 | 2610 | 1790 | 1450 |
| 5 | 2 | 2 | 3 | 3 | 2 | 2 | 12.00 | 1490 | 2610 | 1790 | 1450 |
| 6 | 2 | 1 | 2 | 1 | 2 | 3 | 12.00 | 1490 | 2610 | 1790 | 1450 |
| 7 | 1 | 1 | 3 | 3 | 2 | 2 | 12.00 | 1490 | 2610 | 1790 | 1450 |
| 8 | 1 | 2 | 4 | 5 | 2 | 1 | 12.00 | 1490 | 2610 | 1790 | 1450 |

EXAMPLE 2

Formation and implantation of an articular head spacer implant from the shrunk flat-knitted poly(urethane urea) ribbon of Example 1. An articular implant 2 is excised from the ribbon 1s at bedside. In implantation the implant 2 is disposed, for instance, on the articular head of a proximal interphalangeal joint. The implant 2 is be affixed to the bone by suturing or stapling.

For convenience of handling, a set of implant bodies of varying size and/or form, such as the set 2a, 2b, 2c illustrated in FIGS. 1c-1e, can be provided to the medical profession. The availability of the set allows the physician to select an implant body of suitable size and/or form, and to trim it to make it fit the particular purpose. Implants of standardized size and form that need not to be trimmed can also be provided as single items or in form of sets.

EXAMPLE 3

Shrunk flat-knitted double interlaced poly(urethane urea) ribbon. Yarn: 13 Tex poly(urethane urea) (Artelon®, Artimplant AB, Göteborg, Sweden). Equipment: Comez DNB/EL-800 (Comez s.p.A., Cilavegna, Italy) double needle bed crochet machine, for the production of technical and medical articles. Machine specifications: 15 gauge, 6 weft bars, double needle bed, latch needles. Heat set unit: Comez HSD/800 comprising 2 heat-set cylinders.

A ribbon 200 of two parallel warp knitted layers was knit, a front mesh layer 201, 201', 201", etc. of a thickness of about 1.0 mm, and a rear mesh layer 202, 202', 202", etc., of a thickness of about 1.6 mm. The mesh layers 201, 201', 201"; 202, 202', 202" interlace over bonded sections 203, 203', 203", etc. separated by the non-interlaced or non-bonded sections disposed equidistantly along the ribbon 200 (FIG. 3a). The ribbon 200 is shrunk in the heat set unit to form a shrunk ribbon 200s, in which the elements of the non-shrunk ribbon retain their reference numbers followed by "s" (FIG. 3b). Process parameters: Knitting speed: 26 cm/min; heat set unit speed: 14 cm/min; shrinkage along warp: about 45%; shrinkage across warp: about 45%. Reference numbers 206, 206s indicate separation between non-interlaced or non-bonded sections.

EXAMPLE 4

Figure 4A:
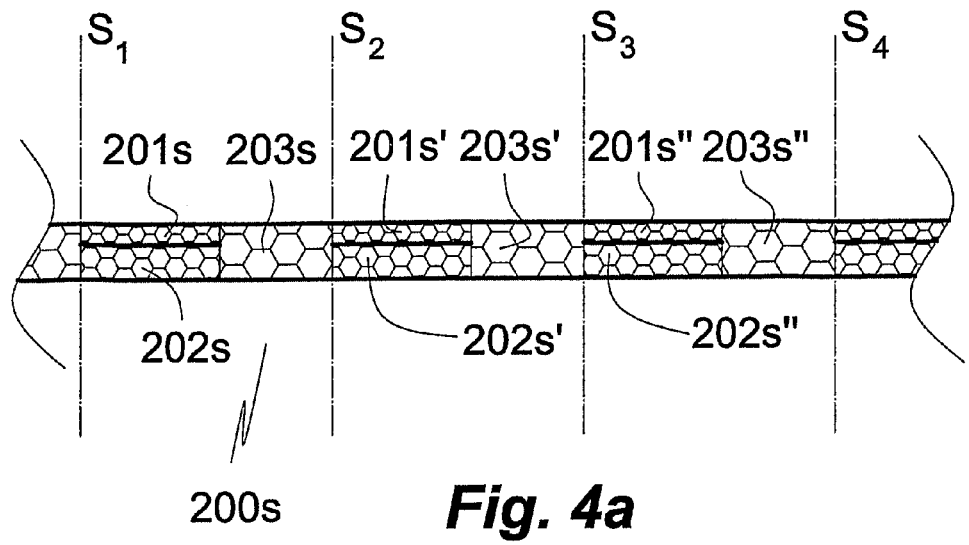
FIG. 4a is the double interlaced flat-knitted ribbon of FIG. 3b, in the same enlarged view, with cutting planes for the excision of the implant of FIG. 4 indicated.
Figures 4, 4B:
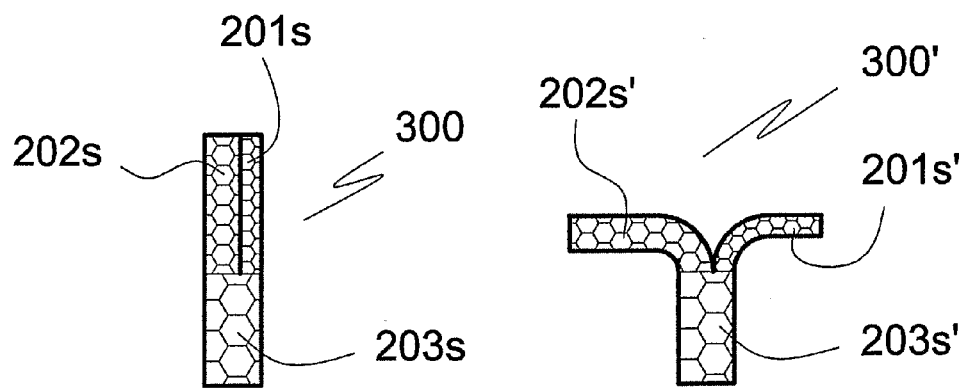
FIG. 4 is a sectional view of an intraarticular spacer implant body of the invention cut out from the flat-knitted ribbon of FIG. 3b, enlarged.
FIG. 4b is an intraarticular spacer implant of the invention formed for implantation from the implant body of FIG. 4, in the same view.
Figure 4C:
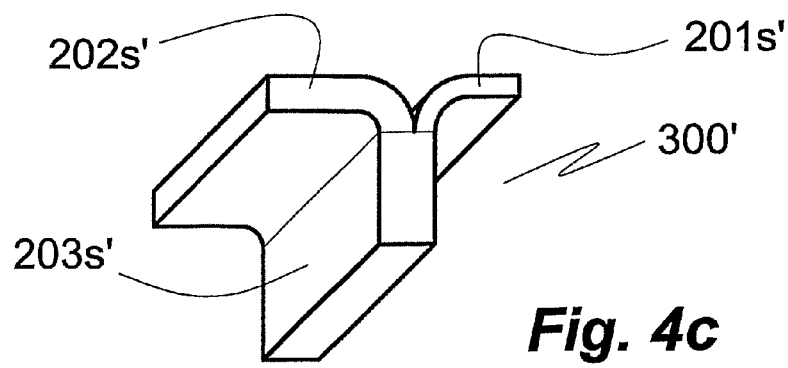
FIG. 4c is a representation of the implant of FIG. 4 in a perspective view.

Formation and implantation of a first articular spacer from the shrunk flat-knitted poly(urethane urea) double interlaced ribbon of Example 3. Implant bodies 300, etc. of identical size and shape, each comprising an interlacing or bonded section, 203s, 203s', 203s" and a pair of adjoining non-interlacing or non-bonded sections, that is a top section 201s, 202s'; 201s", and a bottom section 202s, 202s', 202s" are cut out from the shrunk interlaced ribbon 200s along cutting planes $S_1$, $S_2$, $S_3$, $S_4$, (FIG. 4a). Bending away the non-interlaced or non-bonded sections 201s, 202s of the implant body 300 in opposite directions results in a T-formed articular spacer 300' (FIGS. 4b, 4c) of the general geometric kind disclosed in FIG. 1 of U.S. Pat. No. 7,037,342 B2. Intra-articular implantation of the spacer 300' and fixation is accomplished in a manner substantially corresponding to that disclosed for the known T-formed spacer of U.S. Pat. No. 7,037,342 B2.

EXAMPLE 5

Formation and implantation of a second articular spacer from the shrunk flat-knitted poly(urethane urea) double interlaced ribbon of Example 3. Implant bodies 310 (FIG. 5), etc. of identical size and shape, each comprising an interlacing or bonded section 203s, 203s', 203s", etc. and a pair of adjoining non-interlacing or non-bonded sections, that is a top section 311, 311', etc. and a bottom section 202s, 202s', 202s", etc. are cut out from the shrunk ribbon 200s along cutting lines $S_{10}$, $S_{10}'$, $S_{11}$, $S_{11}'$, $S_{12}'$, $S_{12}"$, $S_{13}'$, $S_{13}"$ etc. (FIG. 5a). Bending away the non-interlaced or non-bonded sections 201s, 202s of the implant body 310 in opposite directions results in a T-formed articular spacer 310' (FIG. 5b) of the general geometric kind disclosed in FIG. 1 of U.S. Pat. No. 7,037,342 B2. Intra-articular implantation of the spacer 310' and fixation is accomplished in a manner substantially corresponding to that disclosed for the known T-formed spacer of U.S. Pat. No. 7,037,342 B2.

EXAMPLE 6

Formation and implantation of a third articular spacer from the shrunk flat-knitted poly(urethane urea) double interlaced ribbon of Example 3. Implant bodies 410 (FIGS. 6, 6b) of identical size and shape, each comprising wings, 412, 413 extending diametrically opposite from a central body 411 are cut out from the shrunk ribbon 200s along cutting lines $S_{20}$, $S_{20}'$, $S_{20}''$, $S_{20}'''$; $S_{21}$, $S_{21}'$, $S_{21}''$ $S_{21}'''$ etc. (FIG. 6a). In addition, material of the interlaced portion extending from the central body 411 in a transverse direction (in respect of the ribbon 200s) has to be removed (cut off) to bring the thickness of portions 414, 415 formed from bonded section 203s to that of the wings 412, 413, which are formed from non-interlaced or non-bonded portions 201s, 201s'.

Implantation of the implant 410 on a head 400 of a joint is illustrated in FIGS. 7a-7c. The central portion of the head 400 is diseased. Some surface areas 402 are entirely lacking cartilage 401 or their cartilage layer is compromised. In addition the subchondral bone of a central area is affected (FIG. 7a). The bone 400 is prepared for implantation by removing diseased cartilage and bone. A shallow depression 405 in the bone 400 in form of the frustrum of a cone is scooped out to remove the diseased bone tissue. The depth and form of the depression 405 matches the portion of the implant's central body 411 extending from the wings 412, 413 towards the smaller circular end face of the central body 411. This portion of the implant 411 is inserted into the depression 405. One flat side of the flexible wings 411, 412 is now in abutment with a bone surface from which diseased cartilage has been removed. The implant 410 is fastened on the bone 400 by biocompatible glue, optionally in combination suturing to adjacent cartilage.

EXAMPLE 7

Shrunk flat-knitted double interlaced poly(urethane urea) ribbon. Yarn: 13 Tex poly(urethane urea) (Artelon®, Artimplant AB, Göteborg, Sweden). Equipment: Comez DNB/EL-800 (Comez s.p.A., Cilavegna, Italy) double needle bed crochet machine, for the production of technical and medical articles. Machine specifications: 15 gauge, 6 guide bars, double needle bed, latch needles. Heat set unit: Comez HSD/800 comprising 2 heat-set cylinders.

A ribbon 600 of two parallel warp knitted layers was knit, a front mesh layer 601, 601', 601", etc. of a thickness of about 1 mm, and a rear mesh layer 602, 602', 602", etc. of same thickness. The mesh layers 601, 601', 601"; 602, 602', 602" interlace over bonded sections 603, 603', 603", etc. separated by the non-interlaced or non-bonded sections disposed equidistantly along the ribbon 600 (FIG. 8a). The ribbon 600 is shrunk in the heat set unit to form a shrunk ribbon 600s, in which the elements of the non-shrunk ribbon retain their reference numbers followed by "s". Process parameters: Knitting speed: $^{18}/_{22}$ cm/min; heat set unit speed: $^{10}/_{12}$ cm/min; shrinkage along warp: about 45%; shrinkage across warp: about 45%. The warp knitting pattern is shown in Table 2. It is a sequence of 120 steps with 8.5 loops/cm for the interlace or bonded and 10 loops/cm for the non-interlaced or non-bonded sections. Four guide bars were employed to produce the ribbon 600 shown in FIG. 8a.

TABLE 2

| Loop row | Binding device movement | | | | | | | | Loops/cm | Alimentation device setting (warp feed) | | |
|---|---|---|---|---|---|---|---|---|---|---|---|---|
| | | 2 | | 4 | 5 | | 7 | | | | | |
| 1 | 2 | 2 | 2 | 2 | 2 | 3 | 2 | 1 | 8.50 | 2050 | 2300 | 2050 |
| 2 | 2 | 1 | 2 | 3 | 2 | 2 | 1 | 1 | 8.50 | 2050 | 2300 | 2050 |
| 3 | 1 | 1 | 2 | 2 | 2 | 1 | 1 | 2 | 8.50 | 2050 | 2300 | 2050 |
| 4 | 1 | 2 | 2 | 1 | 2 | 2 | 2 | 2 | 8.50 | 2050 | 2300 | 2050 |
| 5-56 | | | | | 13x [1-4] | | | | | | | |
| 57 | 2 | 2 | 2 | 2 | 2 | 3 | 2 | 1 | 8.50 | 2050 | 2300 | 2050 |
| 58 | 2 | 1 | 2 | 3 | 2 | 2 | 1 | 1 | 8.50 | 2050 | 2300 | 2050 |
| 59 | 1 | 1 | 3 | 2 | 2 | 2 | 1 | 2 | 10.00 | 1850 | 2300 | 1850 |
| 60 | 1 | 2 | 2 | 2 | 2 | 1 | 2 | 2 | 10.00 | 1850 | 2300 | 1850 |
| 61 | 2 | 2 | 2 | 1 | 2 | 2 | 2 | 1 | 10.00 | 1850 | 2300 | 1850 |
| 62 | 2 | 1 | 2 | 2 | 2 | 3 | 1 | 1 | 10.00 | 1850 | 2300 | 1850 |
| 63 | 1 | 1 | 2 | 3 | 2 | 2 | 1 | 2 | 10.00 | 1850 | 2300 | 1850 |
| 64 | 1 | 2 | 2 | 2 | 2 | 1 | 2 | 2 | 10.00 | 1850 | 2300 | 1850 |
| 65-120 | | | | | 14x [61-65] | | | | | | | |

The invention claimed is:

1. A fibre-based intra-articular spacer stabilized against fraying, comprising:
  two or more layers of flat-knitted thermally shrinkable poly(urethane urea) fabric joined to each other, wherein the two or more layers of flat-knitted poly(urethane urea) fabric each have a warp and a weft and the two or more layers of flat-knitted poly(urethane urea) are crimped in a direction either along the weft or perpendicular to the weft;
  one or more interlaced sections separated by one or more non-interlaced sections of the spacer disposed equidistantly along the intra-articular spacer, wherein the interlaced section extends over the two or more layers of flat-knitted thermally shrinkable poly(urethane urea) fabric;
  a first cut edge at an area of abutment between the one or more interlaced sections and the one or more non-interlaced sections; and
  a second cut edge formed only in the non-interlaced section and in less than all of the two or more layers of flat-knitted thermally shrinkable poly(urethane urea) fabric.

2. The intra-articular spacer of claim 1, wherein the poly(urethane urea) fabric has a glass transition temperature is from 35° C. to 120° C.

3. The intra-articular spacer of claim 2, wherein the glass transition temperature is from 40° C. to 80° C.

4. The intra-articular spacer of claim 1, wherein the fabric has been thermally crimped by at least 10 percent.

5. The intra-articular spacer of claim 4, wherein the fabric has been crimped by 20 percent or more.

6. The intra-articular spacer of claim 4, wherein the fabric has been crimped by 35 percent or more.

7. The intra-articular spacer of claim 1, wherein the thermally shrinkable poly(urethane urea) fabric is a heat-shrinkable poly(urethane urea) fabric.

8. The intra-articular spacer of claim 1, wherein a fibre joins the two or more layers to each other in the one or more interlaced sections and is made of the same material as the knitted-fabric fibre.

9. The intra-articular spacer of claim 1, wherein a fibre joins the two or more layers to each other in the one or more interlaced sections and is made of a material different from the material of the knitted-fabric fibre.

10. The intra-articular spacer of claim 1, wherein the thickness of the two or more layers of knitted fabric is from 0.3 mm to 2.0 mm.

11. The intra-articular spacer of claim 1, wherein the thickness of each of the two or more layers of knitted fabric layer is from 0.3 mm to 2.0 mm.

12. The intra-articular spacer of claim 1, wherein a crimping temperature is a temperature about equal to or higher than the glass transition temperature.

13. The intra-articular spacer of claim 12, wherein the crimping temperature exceeds the glass transition temperature by 15° C. or more.

14. The intra-articular spacer of claim 12, wherein the crimping temperature exceeds the glass transition temperature by 40° C. or more.

15. The intra-articular spacer of claim 1 having the form of a generally T-shaped transverse cross-sectional profile having a central body and wings, wherein the central body corresponds to an interlaced section and the wings correspond to a non-interlaced section with a first wing corresponding to a first layer and a second wing corresponding to a second layer of the non-interlaced section.

16. The intra-articular spacer of claim 15, wherein the central body has an extension in a longitudinal direction of the profile smaller than the extension of one or both wings in the same direction.

17. A fibre-based intra-articular spacer surgical implant stabilized against fraying, comprising:
two or more layers of flat-knitted thermally shrinkable poly(urethane urea) fabric joined to each other, wherein the two or more layers of flat-knitted poly(urethane urea) fabric each have a warp and a weft and the two or more layers of flat-knitted poly(urethane urea) are crimped in a direction either along the weft or perpendicular to the weft;
an interlaced section and a non-interlaced section of the spacer, wherein the spacer has a generally T-shaped transverse cross-sectional profile having a central body and wings, wherein the interlaced section forms the central body and the non-interlaced section forms the wings, such that a first wing is formed of a first layer of the non-interlaced section and a second wing is formed of a second layer of the non-interlaced section; and
wherein the dimensions of the central body is adapted to fit within a corresponding depression at an implant site and is amenable for fastening by a glue or sutures.

18. The intra-articular spacer of claim 17, wherein the poly(urethane urea) fabric has a glass transition temperature from 35° C. to 120° C.

19. The intra-articular spacer of claim 17, wherein the poly(urethane urea) fabric has a glass transition temperature from 40° C. to 80° C.

20. The intra-articular spacer of claim 17, wherein the fabric has been thermally crimped by 45 percent.

21. The intra-articular spacer of claim 17, wherein the thermally shrinkable poly(urethane urea) fabric is a heat-shrinkable poly(urethane urea) fabric.

22. The intra-articular spacer of claim 17, wherein a fibre joins the two or more layers to each other and is of the same material as the knitted-fabric fibre.

23. The intra-articular spacer of claim 17, wherein a fibre joins the two or more layers to each other and is of a material different from the material of the knitted-fabric fibre.

24. The intra-articular spacer of claim 17, wherein a thickness of the fabric is from 0.3 mm to 2.0 mm.

25. The intra-articular spacer of claim 17, wherein a thickness of each of the two or more layers of the knitted fabric is from 0.3 mm to 2.0 mm.

26. The intra-articular spacer of claim 17, wherein a crimping temperature is a temperature about equal to or higher than the glass transition temperature.

27. The intra-articular spacer of claim 17, wherein the central body has an extension in the longitudinal direction of the profile smaller than the extension of one or both of the wings in the same direction.

28. The intra-articular spacer of claim 17, wherein the first wing and the second wing have substantially the same length.

29. The intra-articular spacer of claim 17, wherein the first wing and the second wing have thicknesses that are substantially the same.

* * * * *